United States Patent
Ohkuma

(10) Patent No.: US 6,576,118 B2
(45) Date of Patent: Jun. 10, 2003

(54) CORRECTION DEVICE OF AIR-FUEL RATIO DETECTION APPARATUS

(75) Inventor: Shigeo Ohkuma, Atsugi (JP)

(73) Assignee: Unisia Jecs Corporation, Kanagawa-ken (JP)

( * ) Notice: Subject to any disclaimer, the term of this patent is extended or adjusted under 35 U.S.C. 154(b) by 0 days.

(21) Appl. No.: 09/778,905

(22) Filed: Feb. 8, 2001

(65) Prior Publication Data

US 2001/0052473 A1 Dec. 20, 2001

(30) Foreign Application Priority Data

Feb. 8, 2000 (JP) ........................................ 2000-030677

(51) Int. Cl.$^7$ ............................................. G01N 27/41
(52) U.S. Cl. .................... 205/784.5; 204/401; 204/425; 73/23.32
(58) Field of Search ................................ 204/401, 406, 204/425, 426, 427; 205/784.5; 73/23.32, 23.31; 123/693, 694

(56) References Cited

U.S. PATENT DOCUMENTS

| | | | | |
|---|---|---|---|---|
| 4,532,013 A | * | 7/1985 | Dietz et al. | 204/401 |
| 4,548,179 A | * | 10/1985 | Ninomiya et al. | 123/684 |
| 4,981,125 A | * | 1/1991 | Kato et al. | 123/693 |
| 5,020,499 A | * | 6/1991 | Kojima et al. | 123/479 |
| 5,340,462 A | * | 8/1994 | Suzuki | 123/688 |
| 6,149,786 A | * | 11/2000 | Patrick et al. | 204/401 |
| 6,290,829 B1 | * | 9/2001 | Kato et al. | 204/401 |

FOREIGN PATENT DOCUMENTS

| | | |
|---|---|---|
| JP | 60027751 | 2/1985 |
| JP | 60248040 | 11/1985 |
| JP | 01301939 | 12/1989 |

* cited by examiner

Primary Examiner—Robert J. Warden, Sr.
Assistant Examiner—Kaj K. Olsen
(74) Attorney, Agent, or Firm—Sughrue Mion, PLLC

(57) ABSTRACT

According to the present invention, there is provided: a sensor element including an oxygen concentration detection section consisting of solid electrolyte for outputting a detection signal corresponding to an oxygen concentration in a hollow chamber to which an exhaust of an internal combustion engine is introduced and an oxygen pump section for controlling an electric current to be applied to a solid electrolyte wall that divides the hollow chamber from an exhaust side of the engine so that the oxygen concentration in the hollow chamber becomes a predetermined oxygen concentration, to flow oxygen into/out of the hollow chamber; an air-fuel ratio detection circuit for outputting an air-fuel ratio detection value based on the electric current applied to the solid electrolyte wall by the oxygen pump section; and a pump current cut off circuit for cutting off the power supply to the solid electrolyte wall by the oxygen pump section, and a detection value of air-fuel ratio is corrected based on an output value of the air-fuel ratio detection circuit of when the power supply to the solid electrolyte wall by the oxygen pump section is cut off by the pump current cut off circuit, while detecting the air-fuel ratio over a wide range.

12 Claims, 4 Drawing Sheets

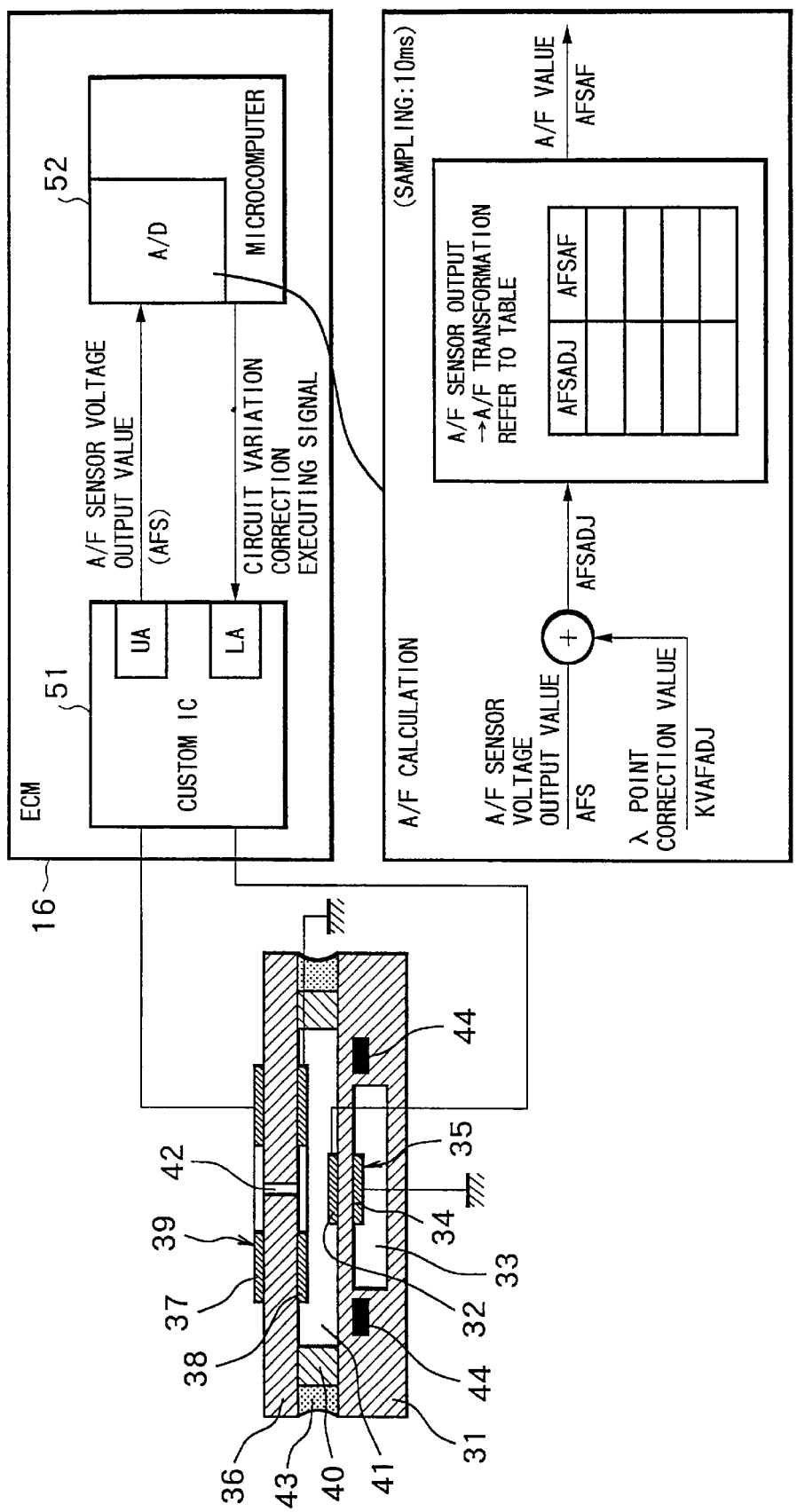

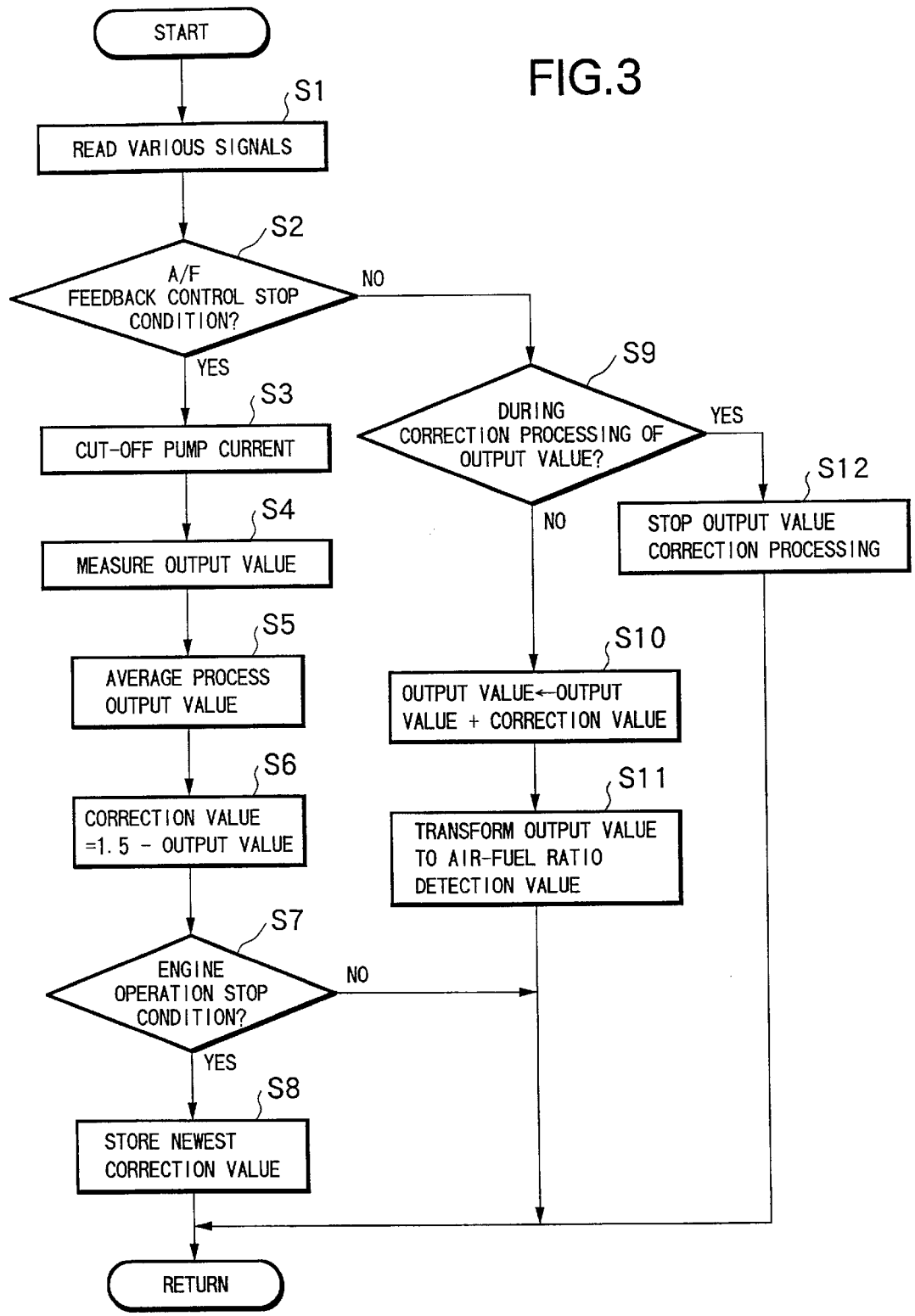

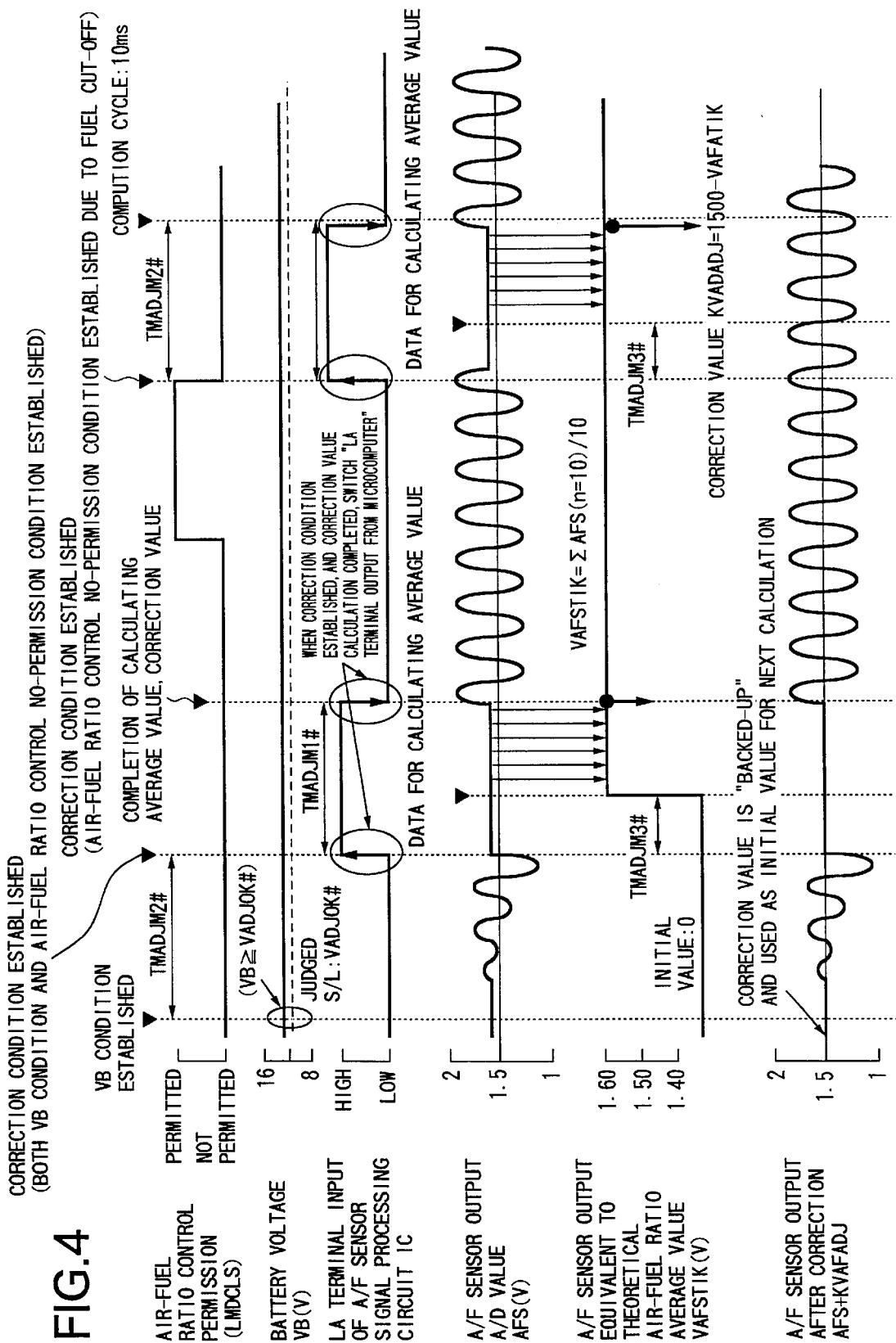

CORRECTION DEVICE OF AIR-FUEL RATIO DETECTION APPARATUS

FIELD OF THE INVENTION

The present invention relates to a correction of an air-fuel ratio detection value to be used when an air-fuel ratio of an internal combustion engine is feedback controlled, in particular, to a technique for maintaining detection accuracy of the air-fuel ratio to a high level.

RELATED ART OF THE INVENTION

Conventionally, there has been known an air-fuel ratio feedback control in which an air-fuel ratio of an engine intake air-fuel mixture is indirectly detected by detecting an oxygen concentration within an engine exhaust by an oxygen sensor, to feedback control a fuel supply quantity so that the air-fuel ratio detected by the oxygen sensor approaches a target air-fuel ratio (refer to Japanese Unexamined Patent Publication No. 60-240840).

In such an air-fuel ratio feedback control, a control in which a target air-fuel ratio is set to a theoretical air-fuel ratio by using the oxygen sensor capable of detecting rich/lean with respective to the theoretical air-fuel ratio, has been generally been performed. However, coping with the recent improvement of exhaust emission characteristic and the increase in demand for improvement of fuel economy, there has been developed a lean combustion engine in which an extremely higher air-fuel ratio (for example, 20–40) compared to the theoretical air-fuel ratio is set to be a target air-fuel ratio. Thus, a wide range air-fuel ratio sensor capable of detecting a wide air-fuel ratio region as also an oxygen sensor, has been utilized.

The air-fuel ratio sensor mentioned above comprises an oxygen concentration detection section consisting of a solid electrolyte for outputting a detection signal corresponding to an oxygen concentration within a hollow chamber to which an exhaust gas from the internal combustion engine is introduced, an oxygen pump section for controlling an electric current to be applied to a solid electrolyte wall that divides the hollow chamber from the exhaust side of the engine, to flow oxygen into/out of the hollow chamber, so that the oxygen concentration in the hollow chamber becomes a predetermined oxygen concentration.

In such a wide range air-fuel ratio detection apparatus, there are some apparatuses that correct output dispersion (inactivity and the like) due to temperature characteristics of the air-fuel ratio sensor (refer to Japanese Unexamined Patent Publication Nos. 60-27751, 1-301939).

However, conventionally, there has not been performed such a correction to dispersion at the manufacture time of circuit for detecting an air-fuel ratio or dispersion of temperature characteristics corresponding to electric current applied to the solid electrolyte (to be referred to pump current hereinafter).

SUMMARY OF THE INVENTION

The present invention has been achieved by paying attention to such conventional problems and aims at correcting dispersion of a detection circuit for detecting an air-fuel ratio corresponding to a pump current of a wide range air-fuel ratio sensor (sensor element), to thereby maintain detection accuracy to a high level.

Another object of the present invention is to perform the correction of the air-fuel ratio when such a correction does not affect an engine operation.

A further object of the present invention is to perform the correction of the air-fuel ratio at high accuracy without any influence by a noise or a transitional variation.

For achieving the above objects, the present invention is constructed as follows.

An oxygen concentration detection section of a sensor element outputs a detection signal corresponding to an oxygen concentration in a hollow chamber to which an exhaust from an internal combustion engine is introduced, an oxygen pump section controls an electric current to be applied to a solid electrolyte wall that divides the hollow chamber from an exhaust side of the engine, to flow oxygen into/out of the hollow chamber, so that the oxygen concentration in the hollow chamber becomes a predetermined oxygen concentration.

An air-fuel ratio detection circuit outputs an air-fuel ratio detection value based on the electric current applied to the solid electrolyte wall by the oxygen pump section.

With the above construction, a power supply to the solid electrolyte wall by the oxygen pump section is cut off by a pump current cut off circuit while detecting an air-fuel ratio over a wide range, and the air-fuel ratio detection value is corrected based on an output value from the air-fuel ratio detection circuit at this time.

According to such a construction, when a normal air-fuel ratio sensor is used, the electric current to be applied to the solid electrolyte wall is controlled by the oxygen pump section so that the oxygen concentration in the hollow chamber becomes an oxygen concentration corresponding to a predetermined air-fuel ratio (typically, a theoretical air-fuel ratio). The direction of applied current is reversed depending on the richer/leaner of an exhaust air-fuel ratio to the predetermined air-fuel ratio. If the exhaust air-fuel ratio is equal to the predetermined air-fuel ratio, the electric current flowing to the solid electrolyte wall corresponds to 0.

Accordingly, when the power supply by the oxygen pump section to the solid electrolyte wall is cut off by the pump current cut off circuit, the air-fuel ratio detected by the detection circuit is to be the predetermined air-fuel ratio.

Therefore, when the power supply to the solid electrolyte wall is cut off, based on a deviation between an output value of the detection circuit and an output value corresponding to the predetermined air-fuel ratio, a correction can be performed on a detection value of air-fuel ratio detected over a wide range at the normal usage time when the pump current of the air-fuel ratio sensor is supplied.

Thus, detection accuracy of air-fuel ratio can be maintained to a high level.

Further, the construction may be such that the air-fuel ratio detection value is corrected under an operation condition that an engine air-fuel ratio feedback control based on the air-fuel ratio detection apparatus is stopped.

According to the above construction, since a detection result of the air-fuel ratio detection apparatus is unnecessary under the operation condition that the engine air-fuel ratio feedback control is stopped, the air-fuel ratio detection value is corrected under such an operation condition, resulting in no influence to the engine operation.

Moreover, the operation condition that the air-fuel ratio feedback control is stopped includes the inactivity of sensor element, so that the correction of detection circuit can be performed under a condition that the exhaust air-fuel ratio cannot be detected.

In the above, the air-fuel ratio detection value may be corrected at the time when a fuel supply to the engine is stopped.

In this way, even when the fuel supply to the engine is stopped at the deceleration time and the like, the air-fuel ratio feedback control is not performed and the detection result of the air-fuel ratio detection apparatus is unnecessary, therefore, the correction of the air-fuel ratio detection value during this time does not affect the engine operation.

Moreover, the air-fuel ratio detection value may be corrected, based on a value obtained by averaging process of the output value of the air-fuel ratio detection circuit of when the power supply to the solid electrolyte wall by the oxygen pump section is cut off.

In this way, by average processing the output value of the detection circuit, the air-fuel ratio detection value can be corrected at high accuracy based on an output value avoiding any influence by a noise or a transitional variation.

Furthermore, a correction value of the air-fuel ratio detection value just before the engine operation stop may be back-up stored to use an initial value for the next operation.

In this way, the correction value of the air-fuel ratio detection value most newly updated during engine operation is used as an initial value when the air-fuel ratio detection value at the next operation is corrected, to thereby ensure a high accurate air-fuel ratio detection from the beginning of engine operation start.

Furthermore, the detection circuit may consists of a current/voltage conversion circuit for converting the supply current to the solid electrolyte wall by the oxygen pump section to a voltage signal and an A/D conversion circuit for converting an output value from the current/voltage conversion circuit to an air-fuel ratio detection value. With this construction, the air-fuel ratio detection value is corrected by comparing the output value of the current/voltage conversion circuit at the time when the power supply to the solid electrolyte wall by the oxygen pump section or the air-fuel ratio detection value converted by the A/D conversion circuit with corresponding reference value.

According to this construction, the detection of air-fuel ratio is performed by converting the supply current to the solid electrolyte wall by the oxygen pump section to the voltage signal by the current/voltage conversion circuit and converting this analog voltage to a digital air-fuel ratio detection value by the A/D conversion circuit utilizing an AND conversion table.

Further, the air-fuel ratio detection value may be corrected by correcting the output value (voltage) of the current/voltage conversion circuit such that the output value and/or the conversion table is corrected so that a deviation between the output value of the current/voltage conversion circuit of when the pump current is cut off and an output value corresponding to the abovementioned predetermined air-fuel ratio becomes smaller. Or, the air-fuel ratio detection value may be corrected by correcting the current/voltage conversion circuit of when the pump current is cut off such that the air-fuel ratio detection value (digital value) of the A/D conversion circuit is corrected so that a deviation between the air-fuel ratio detection value converted by the A/D conversion circuit and the predetermined air-fuel ratio becomes smaller.

Other objects and features of this invention will become understood from the following description with reference to the accompanying drawings.

BRIEF EXPLANATION OF THE DRAWINGS

FIG. 2 is a diagram showing an air-fuel ratio sensor and the peripheral circuits thereof in the embodiment;

FIG. 3 is a flowchart showing a correction control of air-fuel ratio detection value in the embodiment; and FIG. 4 is a time chart showing changes in various statuses at the time of correction control.

PREFERRED EMBODIMENT

Figure 1:
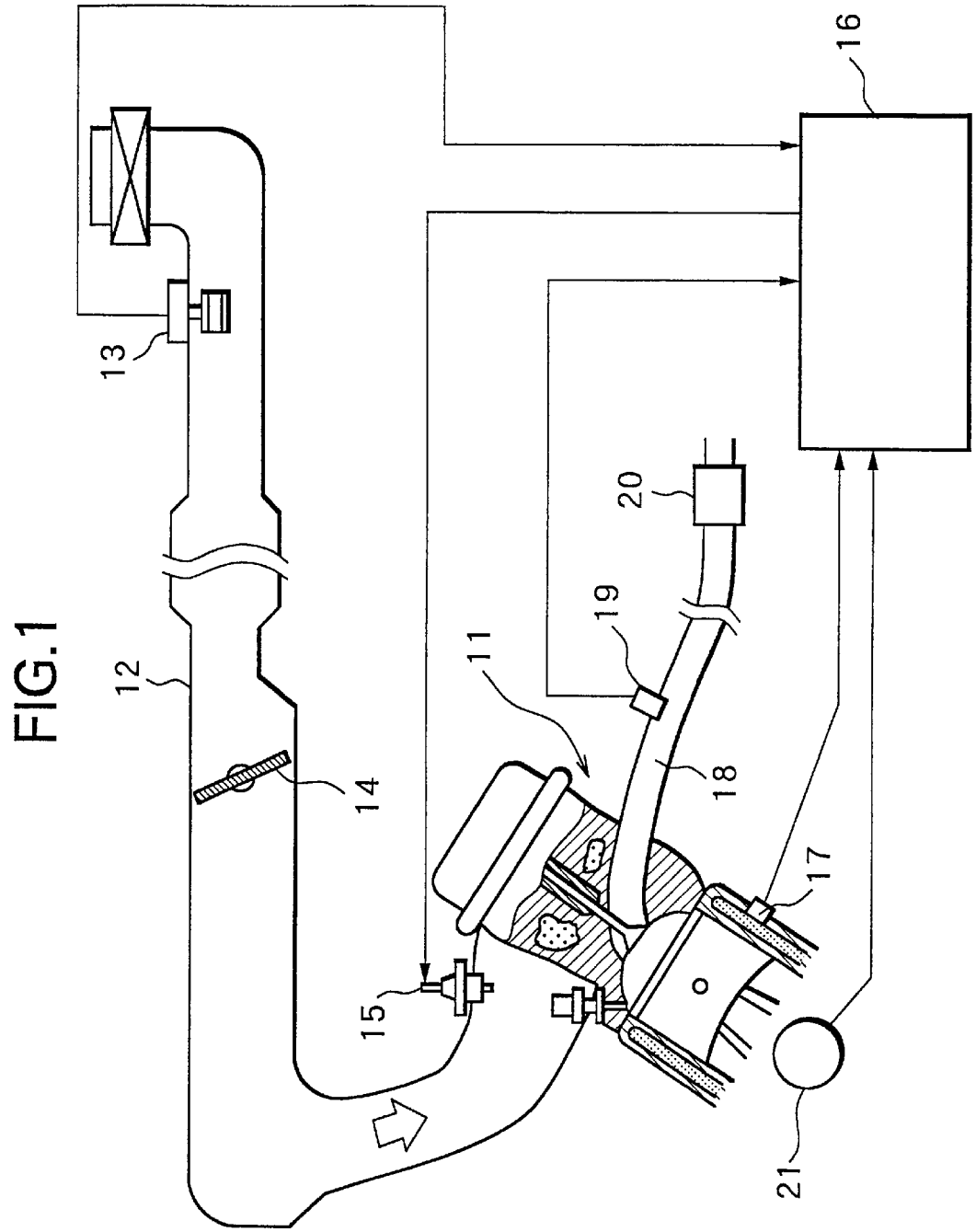
FIG. 1 is a diagram showing a system structure of an embodiment according to the present invention.

An embodiment of the present invention will now be described hereinbelow based on the drawings.

In FIG. 1 showing a system structure of the embodiment, an intake passage 12 of an engine 11 is provided with an air flow meter 13 for detecting an intake air flow amount Qa and a throttle valve 14 for cooperating with an accelerator pedal to control the intake air flow amount Qa, and an electromagnetic type fuel injection value 15 for each cylinder is mounted to a manifold portion on the downstream side.

The fuel injection valve 15 is driven to open by an injection pulse signal from an ECM (engine control module) 16 incorporating therein a microcomputer, to injectingly supply fuel that is sent under pressure from a fuel pump (not shown in the figure) and controlled to a predetermined pressure by a pressure regulator. Further, there is provided a water temperature sensor 17 for detecting a cooling water temperature Tw inside a cooling jacket of the engine 11, and also a wide range air-fuel ratio sensor 19 for linearly detecting an air-fuel ratio of air-fuel mixture in accordance with an oxygen concentration in exhaust of an exhaust passage 18 and a three way catalytic converter 20 for oxidizing CO, HC and reducing $NO_x$ in the exhaust at the downstream side to purify.

A distributor (not shown in the figure) incorporates therein a crank angle sensor 21, and counts up, for a constant time, crank unit angle signals output from the crank angle sensor 21 in synchronous with an engine rotation, or measures the cycle of a crank reference angle signal, to detect an engine rotation speed Ne.

Further, the ECM 16 calculates and controls a fuel injection amount from the fuel injection valve 15 or an ignition timing.

Here, the structure of the wide range air-fuel ratio sensor (sensor element) is described based on FIG. 2.

On a substrate 31 consisting of solid electrolyte material such as zirconia ($ZrO_2$) is provided a plus electrode 32 for measuring an oxygen concentration. Also, an air introduction hole 33 through which air is introduced is formed on the substrate 31 and on this air introduction hole 33 is mounted a minus electrode 34 so as to face the plus electrode 32.

In this way, an oxygen concentration detection section 35 is formed with the substrate 31, the plus electrode 32 and the minus electrode 34.

Furthermore, the air-fuel ratio sensor 19 has an oxygen pump section 39 that is formed by mounting pump electrodes 37 and 38 consisting of a pair of platinum on both surfaces of the solid electrolyte material 36 such as zirconia.

Moreover, the oxygen pump section 39 is laid over the oxygen concentration detection section 35 via a spacer 40 formed in a frame shape with for example alumina, to form a hollow chamber 41 closed between the oxygen concentration detection section 35 and the oxygen pump section 39. Also, an introduction hole 42 for introducing the exhaust to this hollow chamber 41 is formed on the solid electrolyte material 36 of the oxygen pump section 39. Note, a glass made adhesive 43 is fulfilled in the peripheral portion of the spacer 40 to ensure the sealing performance of the hollow chamber 41 and also to adhesively fix the spacer 40 and the substrate 31 to the solid electrolyte material 36. Here, since the spacer 40 and the substrate 31 are simultaneously baked to be coupled, the sealing performance of the hollow chamber 41 is ensured by bonding the spacer 40 and the solid electrolyte material 36. Further, the oxygen concentration detection section 35 incorporates therein a heater 44 for warming-up.

Then, an oxygen concentration within the exhaust introduced to the hollow chamber 41 via the introduction hole 42 is detected based on a voltage of the plus electrode 32. To be specific, an oxygen ion current flows within the substrate 31 in accordance with a concentration difference between oxygen in the atmosphere inside the air introduction hole 33 and oxygen in the exhaust inside the hollow chamber 41. Accompanied with this, a voltage corresponding to the oxygen concentration in the exhaust is generated in the plus electrode 32.

Then, depending on this detection result, a current value to be flown in the oxygen pump section 39 can be variably controlled so as to maintain the ambient inside the hollow chamber 41 to a theoretical air-fuel ratio, to detect the oxygen concentration in the exhaust based on the current value at that time.

Specifically, after the voltage of the plus electrode 32 is subjected to amplification processing by the ECM 16, the amplified voltage is applied between the electrodes 37 and 38 so that the oxygen concentration in the hollow chamber 41 is kept constant.

For example, when an air-fuel ratio in a lean region of a high oxygen concentration in the exhaust is detected, the pump electrode 37 on the outside is made anode and the pump electrode 38 on the hollow chamber 41 side is made cathode to apply the voltage. Then, oxygen (oxygen ion $O^{2-}$) proportional to the current is pumped out from the hollow chamber 41 to the outside. Further, when the applied voltage becomes greater than or equal to a predetermined value, the flowing current reaches a limit value so that the oxygen concentration in the exhaust, in other words, the air-fuel ratio can be detected by measuring this limit current value by the ECM 16.

On the contrary, if the pump electrode 37 is made cathode and the pump electrode 38 anode to pump oxygen into the hollow chamber 41, the air-fuel ratio can be detected in a rich region of a low oxygen concentration of the exhaust.

The ECM 16 comprises an analog control circuit 51 consisting of a custom IC and a microcomputer 52.

The control circuit 51 controls the voltage to be applied to the electrodes 37 and 38 as mentioned above, and has a function of a current/voltage conversion circuit for converting a pump current (limit current) flowing between the electrodes 37 and 38 by the applied voltage to a voltage signal to output this voltage signal to the microcomputer 52 and a function of a pump current cut off circuit for cutting off the pump current by shutting OFF the voltage applied between the electrodes 37 and 37.

On the other hand, the microcomputer 52 has a function of an A/D conversion circuit for converting an output value (voltage) from the control circuit 51 to an air-fuel ratio detection value (digital value) to output this air-fuel ratio detection value and a function for having the control circuit 51 to operate the pump current cut off circuit under a predetermined operating condition, specifically, under a condition that an air-fuel ratio feedback control is stopped, to correct the air-fuel ratio detection value corresponding to variations in the control circuit 51 based on the output value from the control circuit 51 at that time.

Hereinafter, the correction control of the air-fuel ratio detection value will be described based on FIG. 3.

In step 1, various signals for engine operation conditions are read.

In step 2, it is judged whether or not it is an operation condition in which the air-fuel ratio feedback control is to be stopped. For the air-fuel ratio feedback control stop condition, there are, for example, a period of time until the air-fuel ratio feedback control is started from the engine start (the air-fuel ratio sensor may be inactive), a time of when the fuel supply is stopped at the deceleration time, and a high output time. It is preferable to put a short interval from the detection of the air-fuel ratio feedback control stop condition until the operation condition becomes stable under the control stop condition.

If it is judged that it is the air-fuel ratio feedback control stop condition, the control proceeds to step 3 where the pump current cut off circuit inside the control circuit 51 is operated to cut off the pump current of the oxygen pump section 39 in the air-fuel ratio sensor 19.

In step 4, the output value of the current/voltage conversion circuit (in the control circuit 51) under the condition that the pump current is cut off, is measured. To be specific, a predetermined number, for example 10, of output values are sampled for a predetermined time interval.

In step 5, an average value of the output values sampled for the predetermined number is calculated.

In step 6, a deviation between a reference value (1.5 V) equivalent to the theoretical air-fuel ratio corresponding to the pump current of the output value=0 and the average value of the output values is calculated as a correction value KVAFADJ.

In step 7, it is judged whether or not it is an engine operation stop condition (OFF operation of key switch and the like). If it is the engine operation stop condition, the control proceeds to step 8 where the correction value KVAFADJ most newly calculated and updated in step 6 is stored in a back-up memory in order to use the value KVAFADJ as an initial value for the next time.

Further, it is judged in step 2 that it is not the air-fuel ratio feedback control stop condition but the air-fuel ratio feedback control condition, the control proceeds to step 9 where it is judged whether the output value is in the course of the correction calculation.

If it is judged in step 9 that the output value is not in the course of the correction calculation, the control proceeds to step 10 where the correction value KVAFADJ calculated in step 6 is added to an output value AFS from the control circuit 51 to correct the output value.

In step 11, based on the corrected output value AFSADJ, an air-fuel ratio detection value AFSAF (digital value) corresponding to the output value is obtained according to a conversion table.

If it is judged in step 9 that the output value is in the course of the correction calculation, the control proceeds to step 12 where the correction processing of the output value is stopped and the calculation result until this time is annulled.

Variations of various statuses at the correction time are shown in FIG. 4.

In this way, since the self heat of the control circuit 51 and of harness which connects the control circuit 51 and the air-fuel ratio sensor 19, a change in ambient temperature and detection errors of air-fuel ratio caused by variations at manufacture time are obtained as a deviation between the output value of the control circuit 51 in a temporary stoichiometric status of when the pump current is cut off, and a reference value equivalent to the theoretical air-fuel ratio and the correction is performed so as to reduce the deviation, the detection of the air-fuel ratio can be maintained over a wide range at high accuracy.

Further, if the correction is performed to such as the temperature change of the control circuit 51 and the like according to the present invention, and also the correction is performed to the temperature change of the abovementioned conventional air-fuel ratio sensor (sensor element), further high accurate air-fuel ratio detection can be ensured.

Note, according to the abovementioned embodiment, the construction has been such that the output value (voltage) of the control circuit 51 is corrected based on the deviation, however, the conversion table (correspondence between the output value and the air-fuel ratio detection value) may be corrected based on the deviation. Further, the construction may be such that a deviation between the air-fuel ratio detection value converted by the conversion table when the pump current is cut off, and the theoretical air-fuel ratio is calculated and the air-fuel ratio detection value detected when the normal pump current is supplied is corrected based on this deviation.

The entire contents of Japanese Patent Application No. 2000-030677, filed on Feb. 8, 2000, are incorporated herein by reference.

What we claimed:

1. An air-fuel ratio detection apparatus having correction control and being operative to receive the exhaust of an internal combustion engine, comprising:

a sensor element including an oxygen pump section, said pump section having a first solid electrolyte portion forming a wall that divides an exhaust exposed side from a hollow chamber into which the exhaust from the internal combustion engine is introduced from the exhaust exposed side, and including an oxygen concentration detection section, said detection section having a second solid electrolyte portion that is disposed between said hollow chamber and a source of air, said detection section being operative for outputting a detection signal corresponding to an oxygen concentration in said hollow chamber for controlling a current to be applied to said first solid electrolyte portion so that the oxygen concentration in the hollow chamber becomes a predetermined oxygen concentration, to cause the flow oxygen into/out of the hollow chamber;

an air-fuel ratio detection circuit for outputting an air-fuel ratio detection value based on the current applied to the first solid electrolyte portion by said oxygen pump section;

a pump current cut off circuit for cutting off a power supply to the first solid electrolyte portion by said oxygen pump section; and an air-fuel ratio detection value correction section for correcting a detection value of air-fuel ratio based on an output value from said air-fuel ratio detection circuit at a time when the power supply to the first solid electrolyte portion by said oxygen pump section is cut off by said pump current cut off circuit.

2. An air-fuel ratio detection apparatus according to claim 1, wherein said air-fuel ratio detection value correction section is configured to correct said air-fuel ratio detection value under a condition that an air-fuel ratio feedback control of the engine based on said air-fuel ratio detection value is stopped.

3. An air-fuel ratio detection apparatus according to claim 2, wherein said air-fuel ratio detection value correction section is configured to correct said air-fuel ratio detection value when a fuel supply to the engine is stopped.

4. An air-fuel ratio detection apparatus according to claim 1, wherein said air-fuel ratio detection value correction section is configured to correct said air-fuel ratio detection value based on the output value that is obtained by average processing a plurality of measured values from the detection circuit when the power supply to the first solid electrolyte portion by said oxygen pump section is cut off.

5. An air-fuel ratio detection apparatus according to claim 1, wherein said air-fuel ratio detection value correction section back-up is configured to store a correction value, comprising said air-fuel ratio detection value obtained just before the engine operation is stopped, for use as an initial correction value for a next engine operation time.

6. An air-fuel ratio detection apparatus according to claim 1, wherein said detection circuit comprises a current/voltage conversion circuit for converting a supply current to the solid electrolyte wall by said oxygen pump section to a voltage signal, and an A/D conversion circuit for converting an analog output value from said current/voltage conversion circuit to an air-fuel ratio detection value, and said air-fuel ratio detection value correction section is configured to compare one of an analog output value of said current/voltage conversion circuit when the power supply to the solid electrolyte wall by said oxygen pump section is cut off or a digital air-fuel ratio detection value converted by said A/D conversion circuit with a corresponding reference value, to correct said air-fuel ratio detection value.

7. A method of correcting an air-fuel ratio detection value that is determined on the basis of an output of a sensor element having a solid electrolyte with a first electrolyte portion and a second electrolyte portion, said first and second portions defining an oxygen pump section and a oxygen concentration detection section, respectively, comprising the steps of:

outputting a detection signal corresponding to an oxygen concentration in a hollow chamber to which an exhaust from an internal combustion engine is introduced by the oxygen concentration detection section;

controlling an electric current to be applied to said first electrolyte portion, which forms a solid electrolyte wall that divides said hollow chamber from an exhaust side of the engine so that the oxygen concentration in the hollow chamber becomes a predetermined oxygen concentration, to flow oxygen into/out of the hollow chamber by an oxygen pump section of the sensor element;

outputting an air-fuel ratio detection value from an air-fuel ratio detection circuit based on an electric current applied to the solid electrolyte wall by said oxygen pump section;

establishing a condition wherein the supply of power to the solid electrolyte wall by said oxygen pump section is cut-off; and correcting a detection value of the air-fuel ratio based on an output value from said air-fuel ratio detection circuit determined on the basis of said condition that the supply of power to the solid electrolyte wall by said oxygen pump section is cut off.

8. A correction method of an air-fuel ratio detection value according to claim 7, wherein said air-fuel ratio detection value is corrected under a condition that an air-fuel ratio feedback control of the engine based on said air-fuel ratio detection value is stopped.

9. A correction method of an air-fuel ratio detection value according to claim 8, wherein said air-fuel ratio detection value is corrected when a fuel supply to the engine is stopped.

10. A correction method of an air-fuel ratio detection value according to claim 7, further comprising obtaining a correction for said air-fuel ratio detection value based on the output value which is obtained by average processing a plurality of measured values from a detection circuit at a time when a power supply to the solid electrolyte wall by said oxygen pump section is cut off.

11. A correction method of an air-fuel ratio detection value according to claim 7, further comprising back-up storing a correction value of said air-fuel ratio detection value, obtained just before the engine operation is stopped, for use as an initial correction value for the next engine operation time.

12. A correction method of an air-fuel ratio detection value according to claim 7, further comprising converting supply current to the solid electrolyte wall by said oxygen pump section to a voltage signal, and also converting an analog output value to a digital air-fuel ratio detection value, and correcting said air-fuel ratio detection value by comparing one of the analog output value at a time when power is supplied to the solid electrolyte wall by said oxygen pump section or the digital air-fuel ratio detection value with a corresponding reference value.

* * * * *